United States Patent
Dunlop

(10) Patent No.: US 9,911,632 B2
(45) Date of Patent: Mar. 6, 2018

(54) MULTIPLE PART DECORATION SYSTEM AND METHOD

(71) Applicant: ATS Automation Tooling Systems Inc., Cambridge (CA)

(72) Inventor: Joel Anthony Patrick Dunlop, Cambridge (CA)

(73) Assignee: ATS Automation Tooling Systems Inc., Cambridge (CA)

( * ) Notice: Subject to any disclaimer, the term of this patent is extended or adjusted under 35 U.S.C. 154(b) by 0 days.

(21) Appl. No.: 14/521,639

(22) Filed: Oct. 23, 2014

(65) Prior Publication Data

US 2016/0114595 A1   Apr. 28, 2016

Related U.S. Application Data

(60) Provisional application No. 61/894,571, filed on Oct. 23, 2013.

(51) Int. Cl.
*H01L 21/67* (2006.01)
*B41F 15/18* (2006.01)
(Continued)

(52) U.S. Cl.
CPC ........ *H01L 21/67259* (2013.01); *B41F 15/18* (2013.01); *B41F 33/0036* (2013.01);
(Continued)

(58) Field of Classification Search
CPC ......... H01L 21/67282; H01L 21/67259; H01L 21/67333; H01L 22/12; B41F 15/18;
(Continued)

(56) References Cited

U.S. PATENT DOCUMENTS 3,243,178 A   3/1966   Williamson et al.
4,237,598 A   12/1980  Williamson
(Continued)

FOREIGN PATENT DOCUMENTS

WO   WO 03/092069   *   6/2003

OTHER PUBLICATIONS

Canadian Intellectual Property Office, International Search Report and Written Opinion of the International Searching Authority for PCT Appln. No. PCT/CA2014/051022, dated Jan. 8, 2015.

*Primary Examiner* — Justin Olamit
(74) *Attorney, Agent, or Firm* — Gowling WLG (Canada) LLP; Neil Henderson

(57) ABSTRACT

According to an aspect herein, there is provided a method of decorating multiple parts, the method includes: loading a plurality of parts onto a pallet; registering location of each of the plurality of parts in relation to the pallet; registering location of each of the plurality of parts with each of a plurality of templates; decorating the plurality of parts using the plurality of templates; and inspecting the decorated parts to monitor for defects. According to another aspect herein, there is provided a method of decorating a part, the method includes: positioning a part for decoration; starting a decoration process for the part; and adjusting one or more parameters of the decoration process during the decoration process based on predetermined characteristics of the part or the decoration to provide for enhanced print coverage or quality.

16 Claims, 9 Drawing Sheets

(51) Int. Cl.
  *B41F 33/00* (2006.01)
  *G01N 21/956* (2006.01)
  *G01N 21/88* (2006.01)
  *H01L 21/673* (2006.01)

(52) U.S. Cl.
  CPC ....... *G01N 21/8803* (2013.01); *G01N 21/956* (2013.01); *H01L 21/67282* (2013.01); *B41P 2215/11* (2013.01); *H01L 21/67333* (2013.01)

(58) Field of Classification Search
  CPC .... B41F 15/26; B41F 19/005; B41F 33/0036; B41P 2215/11; B41P 2215/112; B41P 2215/114
  See application file for complete search history.

(56) References Cited

U.S. PATENT DOCUMENTS

| | | | |
|---|---|---|---|
| 4,750,419 A | 6/1988 | Meredith | |
| 5,329,690 A * | 7/1994 | Tsuji | B23P 21/00 29/430 |
| 5,932,119 A * | 8/1999 | Kaplan | B23K 26/032 219/121.68 |
| 6,567,162 B2 | 5/2003 | Koren et al. | |
| 7,322,083 B2 | 1/2008 | Parmenter et al. | |
| 7,354,538 B2 | 4/2008 | Semersky et al. | |
| 7,841,079 B2 * | 11/2010 | Inoue | H05K 3/303 29/739 |
| 9,126,398 B2 * | 9/2015 | Gray | H05K 3/1216 |
| 2013/0110436 A1 * | 5/2013 | Ohta | H04Q 9/00 702/81 |

* cited by examiner

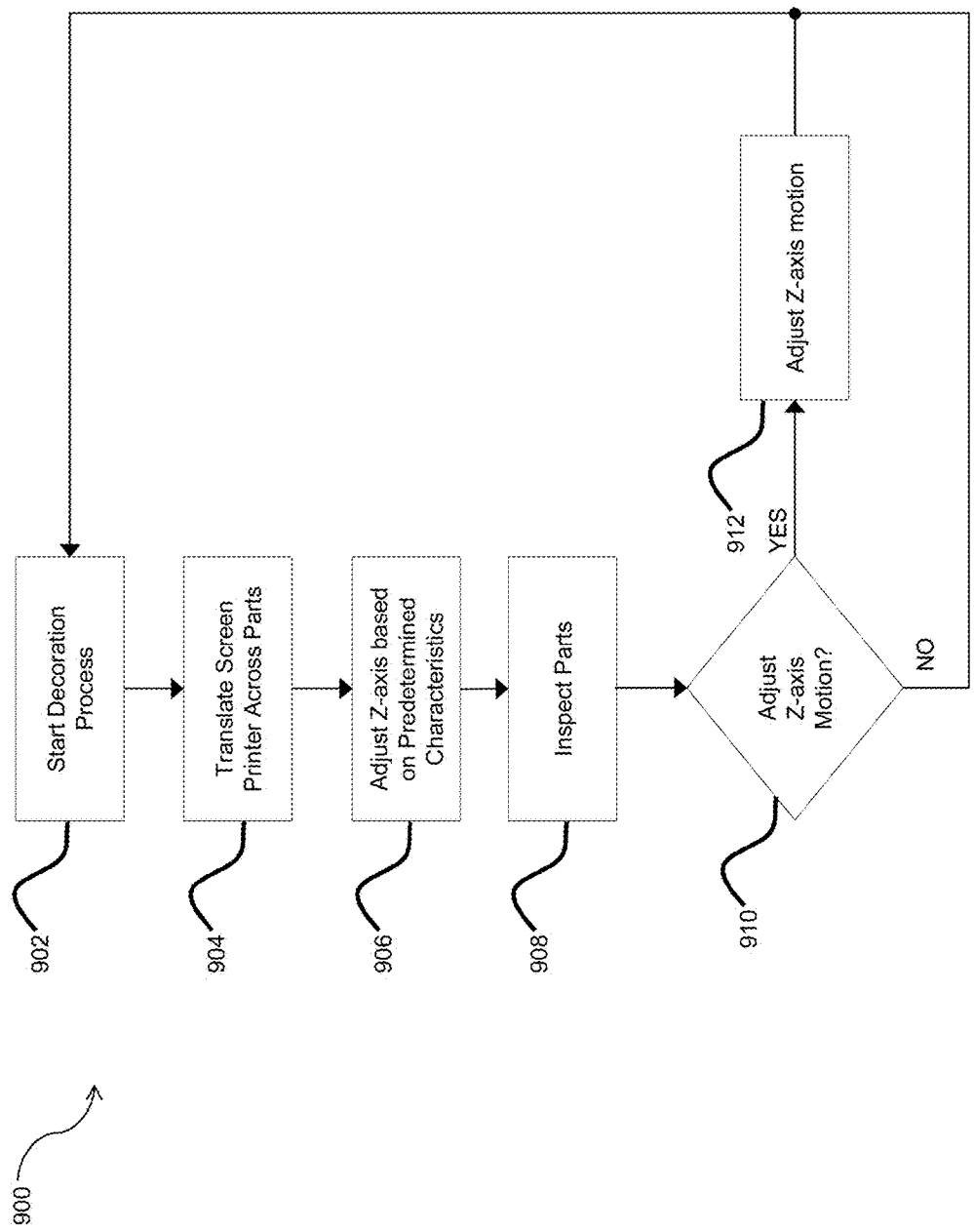

MULTIPLE PART DECORATION SYSTEM AND METHOD

CROSS REFERENCE TO RELATED APPLICATIONS

This application claims the benefit of priority of U.S. Provisional Patent Application No. 61/894,571 filed Oct. 23, 2013, which is hereby incorporated by reference.

FIELD

The current disclosure is generally directed at a decoration system for use with conveyor systems and more specifically, at a multiple part decoration system and method.

BACKGROUND

In the manufacture of modern electronics and other products, it can be important to provide appropriate markings or decorations on parts of the products such as, for example, watch faces, phone faces, transparent parts or the like. In conventional systems, parts are transported on a fixture or pallet through successive processing stations by a conveyor or transport system. Different decorative features or portions may be applied at successive stations. The transport system can be a dial indexer to which the fixtures are attached or some other pallet motion system, or conveyor system with repeatable motion such as, but not limited to, the Supertrak™ system provided by ATS Automation Tooling Systems of Cambridge, Canada.

In conventional decoration systems, the parts are processed in one or more passes where additional layers of decoration are applied on each pass, typically with parts unloaded and dried between passes. This may be very time consuming.

Therefore, there is a need for an improved decoration system and method which overcomes at least some of the disadvantages of current systems.

SUMMARY

It is an object of the present disclosure to obviate or mitigate at least one disadvantage of previous decoration systems.

According to an aspect herein, there is provided a method of decorating multiple parts, the method includes: loading a plurality of parts onto a pallet; registering location of each of the plurality of parts in relation to the pallet; registering location of each of the plurality of parts with each of a plurality of templates; decorating the plurality of parts using the plurality of templates; and inspecting the decorated parts to monitor for defects.

In a particular case, the method also includes providing feedback from the inspecting to the registering location of each of the plurality of parts in relation to the pallet and with each of the plurality of templates.

In another particular case, registering location of each of the plurality of parts and registering location of each of the plurality of parts with each of the plurality of templates includes visual or mechanical registration.

In yet another particular case, registering location of each of the plurality of parts includes: locating reference features on each of the plurality of parts; locating reference features on the pallet; and aligning the respective reference features to position each of the plurality of parts in relation to the pallet. In further cases, the method also includes adjusting the alignment based on feedback from the inspecting in order to compensate for defects or variance In yet another particular case, registering location of each of the plurality of parts with each of the plurality of templates includes: locating reference features on each of the plurality of templates; locating reference features on the pallet or on each of the plurality of parts; and aligning the respective reference features to align each of the plurality of templates in relation to each of the plurality of parts. In further cases, the method also includes adjusting the alignment based on feedback from the inspecting in order to compensate for defects or variance.

In yet another particular case, the decorating includes: monitoring the decorating; and adjusting one or more parameters of the decorating during the decorating to provide for enhanced print coverage. In further cases, the adjusting one or more parameters includes adjusting off-contact during decorating.

In yet another particular case, the inspecting includes: providing predetermined illumination characteristics; capturing images with a plurality of cameras; and analyzing the images.

According to another aspect herein, there is provided a method of decorating a part, the method includes: positioning a part for decoration; starting a decoration process for the part; and adjusting one or more parameters of the decoration part during the decoration process based on predetermined characteristics of the part or the decoration to provide for enhanced print coverage or quality.

In a particular case, the adjusting one or more parameters includes adjusting a distance of a printing mechanism from the part during the decoration process.

In another particular case, the method also includes: inspecting the decoration of the parts; and updating the predetermined parameters based on the inspection of the decoration of the parts.

According to yet another aspect herein, there is provided a system of decorating multiple parts, the system includes: a loading station for loading a plurality of parts onto a pallet; a registration station for registering a location of each of the plurality of parts in relation to the pallet and for registering a location of each of the plurality of parts with each of a plurality of templates; a decoration station for decorating the plurality of parts using the plurality of templates; and an inspection station for inspecting the decorated parts to monitor for defects.

In a particular case, the inspection station provides feedback from the inspecting to the registration station regarding the registering location of each of the plurality of parts in relation to the pallet and with each of the plurality of templates.

In another particular case, registering the location of each of the plurality of parts by the registration station further includes: locating reference features on each of the plurality of parts; locating reference features on the pallet; and aligning the respective reference features to position each of the plurality of parts in relation to the pallet. In further cases, the registration station adjusts the alignment based on feedback from the inspecting at the inspection station in order to compensate for defects.

In yet another particular case, registering the location of each of the plurality of parts with each of the plurality of templates by the registration station further includes: locating reference features on each of the plurality of templates; locating reference features on the pallet or on each of the plurality of parts; and aligning the respective reference features to align each of the plurality of templates in relation to each of the plurality of parts. In further cases, the registration station adjusts the alignment based on feedback from the inspecting at the inspection station in order to compensate for defects.

In yet another particular case, the decorating by the decoration station includes: monitoring the decorating; and adjusting one or more parameters of the decorating during the decorating to provide for enhanced print coverage.

According to yet another aspect herein, there is provided a system of decorating a part, the system includes: a registration station configured to position a part for decoration; a decoration station, the decoration station configured to: start a decoration process for the part; and adjust one or more parameters of the decoration process during the decoration process based on predetermined characteristics of the part or the decoration to provide for enhanced print coverage or quality.

In a particular case, the decoration station adjusts the one or more parameters by adjusting a distance of a printing mechanism from the part during the decoration process.

In another particular case, the system also includes an inspection station configured to inspect the decoration of the parts, and wherein the decoration station updates the predetermined characteristics based on the inspection of the decoration of the parts.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures:

FIG. 9 is a flowchart outlining an embodiment of a method for controlling decoration parameters during decoration.

DETAILED DESCRIPTION

The disclosure is generally directed at a method and system for decorating multiple parts, typically using a conveyor system. The system and method are intended to more efficiently perform the decoration function, in some cases, without needing to remove the parts from the conveyor system between subsequent passes.

Figure 1:
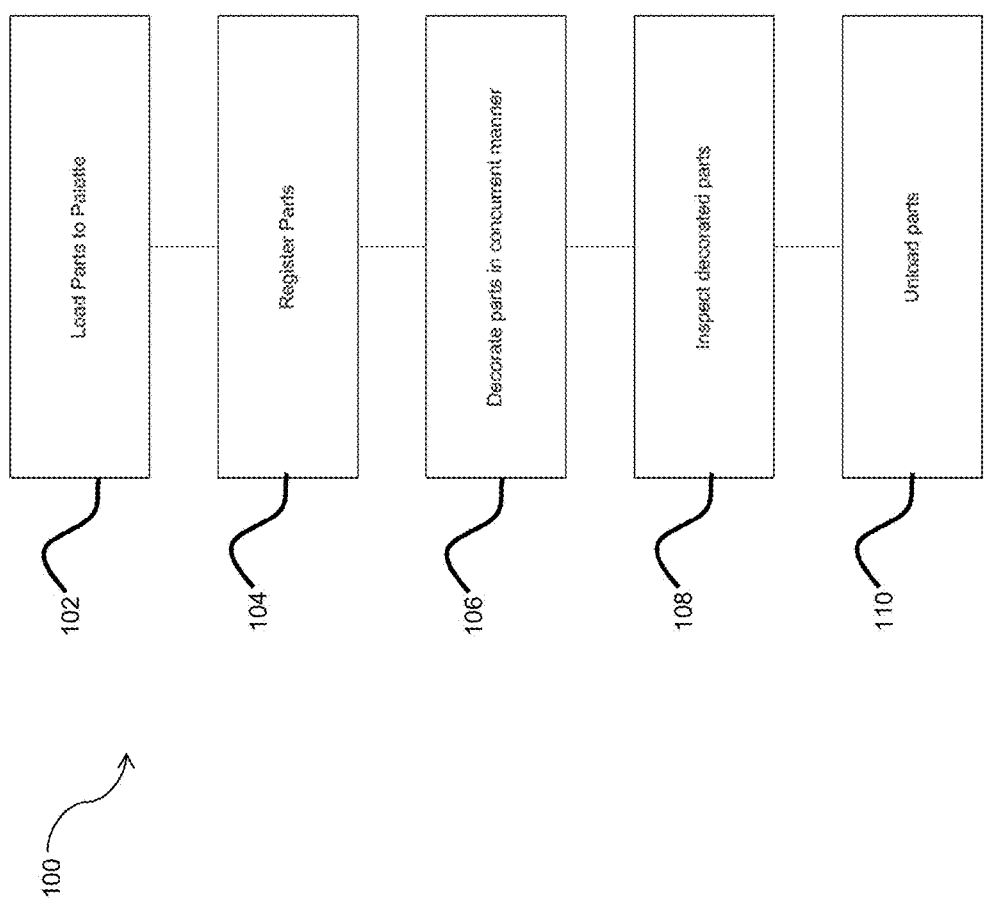
FIG. 1 is a flowchart outlining an embodiment of a method of multi-part decoration.

Turning to FIG. 1, a flowchart of an embodiment of a method 100 for a multiple part (sometimes called multi-part) decoration system is shown. In particular, an embodiment is intended to provide decoration for multiple parts on a conveyor system. In a particular case, instead of having the parts individually placed on the conveyor system, the multiple parts may also be assembled as a whole item for decoration using the same conveyor system. The method 100 is generally intended to provide high precision, including precise registration of decoration to each part, while processing multiple parts concurrently using a multi-image printing template.

Figure 2:
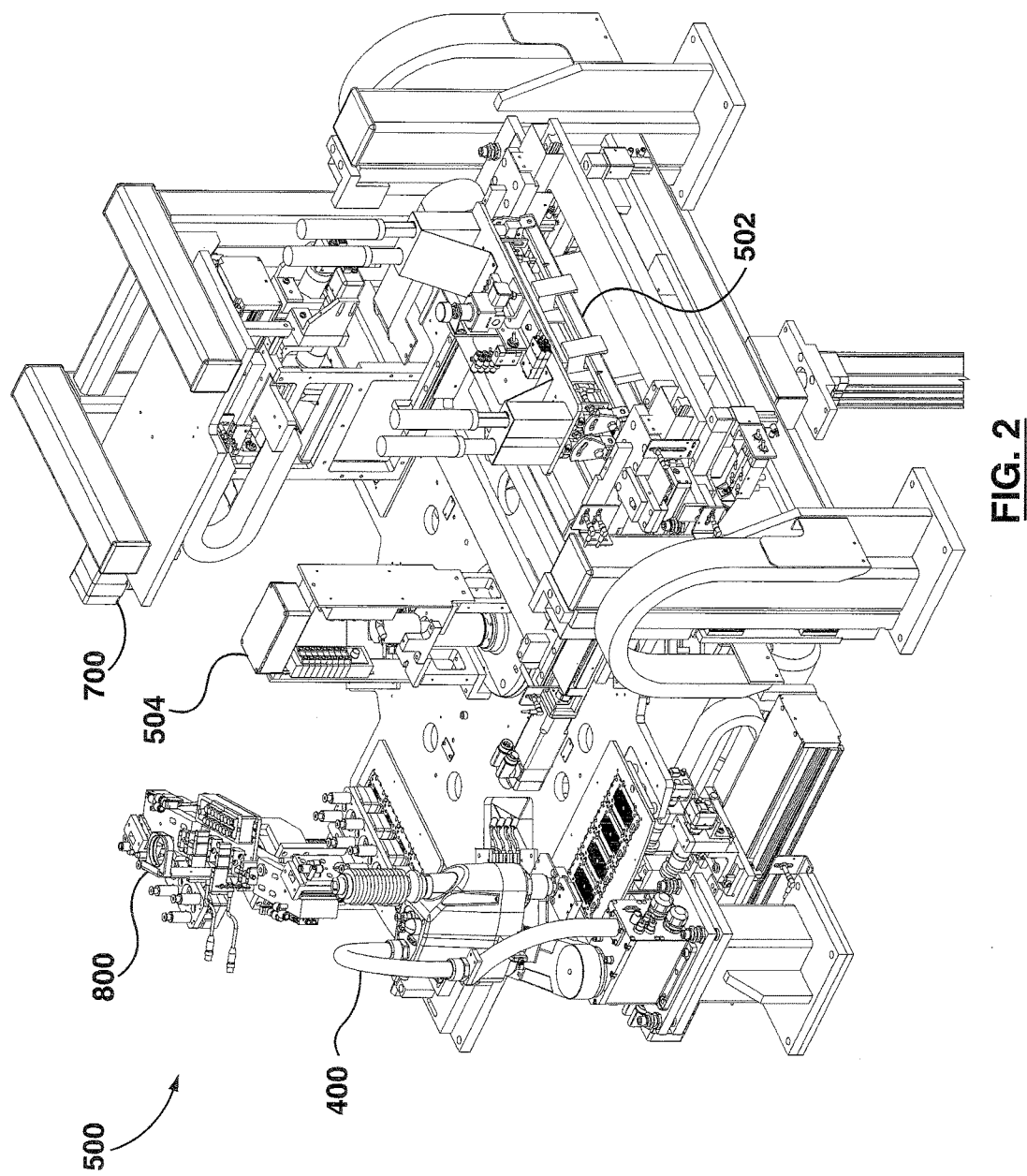
FIG. 2 is a perspective view of an embodiment of a multi-part decoration system.

As shown in FIG. 1, the method 100 includes: load multiple parts to pallet (102); register parts to the pallet and in relation to the decoration module (104); decorate multiple parts at substantially the same time and/or in the same printing process (106); inspect the decorated parts and provide feedback to decoration module for adjustments (108); and unload the decorated parts (110). The following description provides additional detail on each of the aspects of this method. The method 100 can be performed by, for example, a multi-part decoration system 500 as shown in FIG. 2, according to one embodiment.

At 102, the multiple parts are loaded 10 into or onto a pallet. It will be understood that the multiple parts could be a final product, a part for further assembly, or a sub-assembly or the like. The way in which the parts are loaded may be by using typical automation part transfer mechanisms or the like. Understanding that the loading of parts onto the pallet is for the decoration of these parts, the parts are placed in an approximate location for processing within the pallet as understood with respect to the decoration template and the like, as will be discussed.

Figure 3:
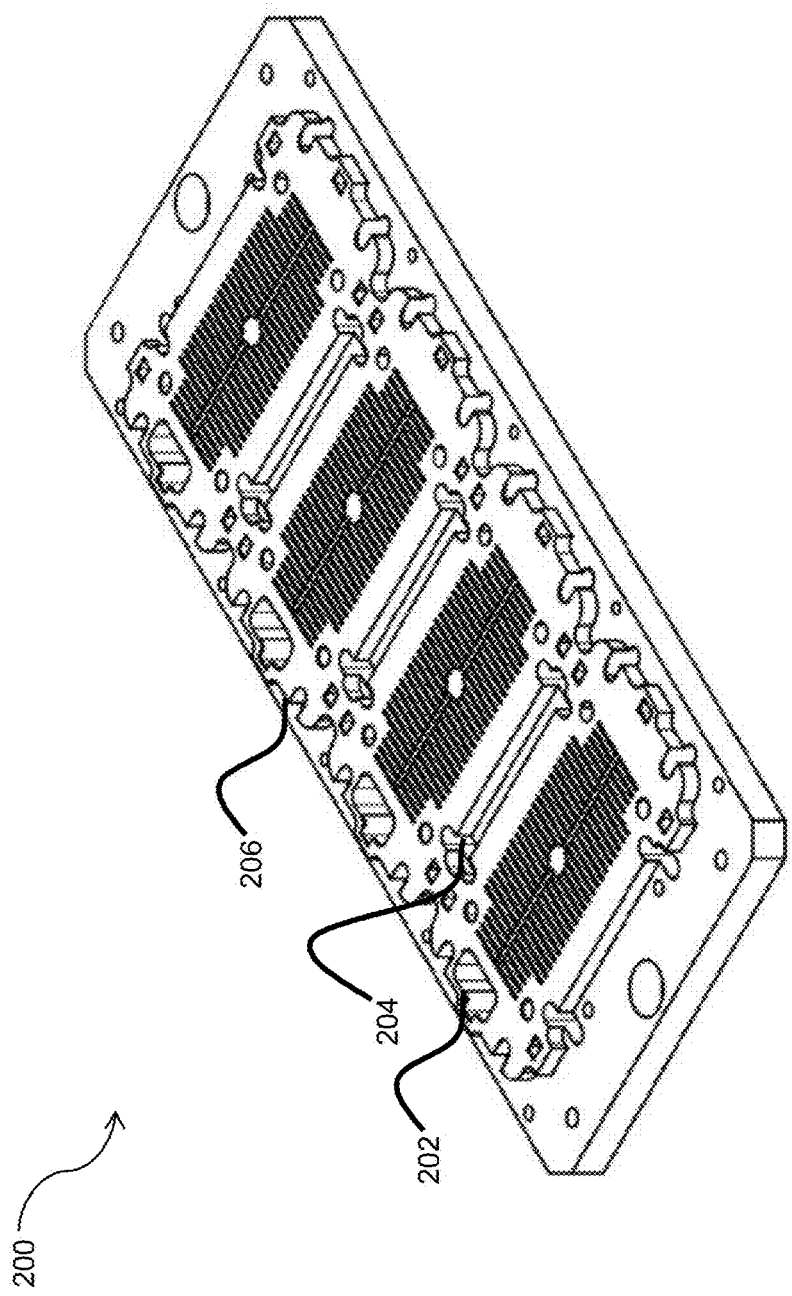
FIG. 3 is a perspective view of an embodiment of a multi-part pallet.

An embodiment of a pallet 200 is shown in FIG. 3. In this case, the pallet provides locations for four parts to be processed at a decoration module in a single printing application.

In some cases, the pallet 200 incorporates vacuum fixtures 202 which allow the parts to be held in position by a vacuum. These fixtures may include apertures 204 providing accessibility to edge features of the part which may be used for part registration. Examples of apertures include view ports for imaging or tool clearances for tools used to engage the parts for loading, unloading and/or mechanical registration of parts or a combination of ports and tool clearances. In another embodiment, the fixture may be a mask support surrounding the parts in order to reduce the deflection of the template outside of the area of the parts (e.g. print screen deflection in the case of screen printing). This provides an advantage of reducing wear on the tooling but is also useful in controlling coverage where decoration extends to the edges of the parts possibly including edge contours. Fixtures may also include visual datums 206 so that parts can be registered using relative alignment of the part to the fixture as discussed below.

Figure 4:
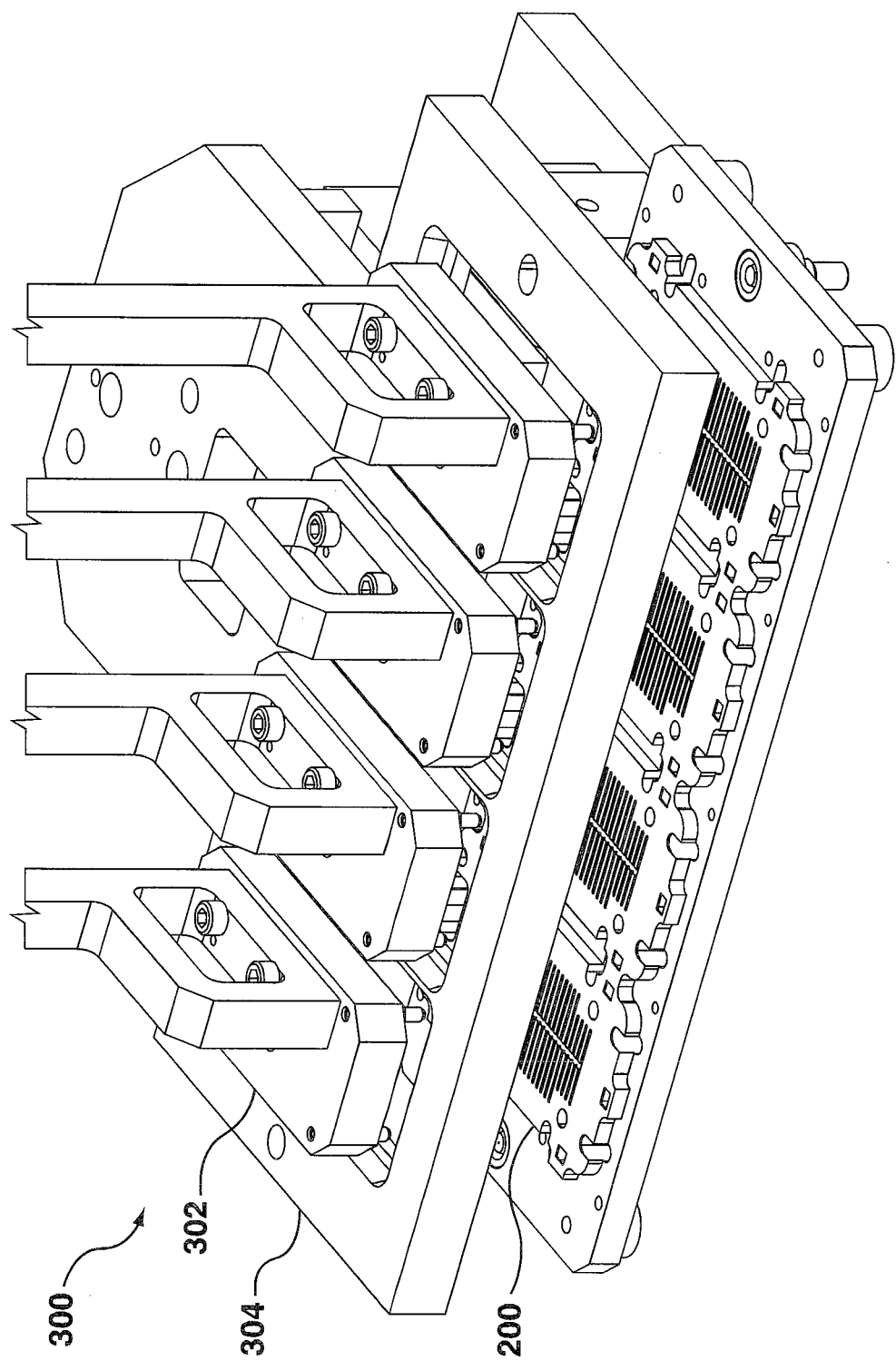
FIG. 4 is a perspective view of an embodiment of a multi-part registration mechanism.

At 104 in the method 100 of FIG. 1, after loading the parts onto the pallet, the parts are registered with respect to the fixtures, or with respect to their locations within the pallet, so that the decoration system recognizes the location of parts within the pallet. An embodiment of a mechanical registration assembly 300 is shown in FIG. 4.

Registration is performed, in some cases, with the assistance of a registration mechanism, such as, but not limited to, a vision system, a 'picture frame' or similar mechanical reference which is placed over the conveyor system, locating pins which are inserted through the fixture, or the like. These registration mechanisms are intended to allow each part to be individually registered so that variations in part dimensions, fixture placement and decoration templates may be accommodated within the decoration system or by the decoration apparatus on a part by part basis.

In order to enable some modes of mechanical registration, parts may be handled in the registration station by a planar vacuum tool, or gripper 302, which permits the part to slide on the gripper when driven by mechanical datum; for example, the gripper may comprise a low friction surface made from a non-abrasive material such as Delrin™.

Mechanical registration may also entail engaging the edges of parts with mechanical features, for example a corner-crowd mechanical datum 304, within the pallet or the registration system which drive the part to a repeatable position defined by the tooling or registration system. These mechanical features may engage the edges of the part, sliding the part to a fixed, known or expected position while it is either held on the pallet or by the vacuum tool. As would be understood, the vacuum tool 302 may be placed above the pallet in an overhead position. In one example, the vacuum tool 302 may be a mechanical device above the plane of the pallet which may be fixed or, if needed, moved into position during the registration stage. Alternately, pins or other details which may be inserted through the pallet during registration. Depending on the actuation of the registration process, parts are either pressed against datum points or datum points are pressed against the part in order to establish a repeatable part position. Typically, there are three (3) datum points although the fixture may be in the form of the vacuum gripper which drives parts to a common center.

Figure 5:
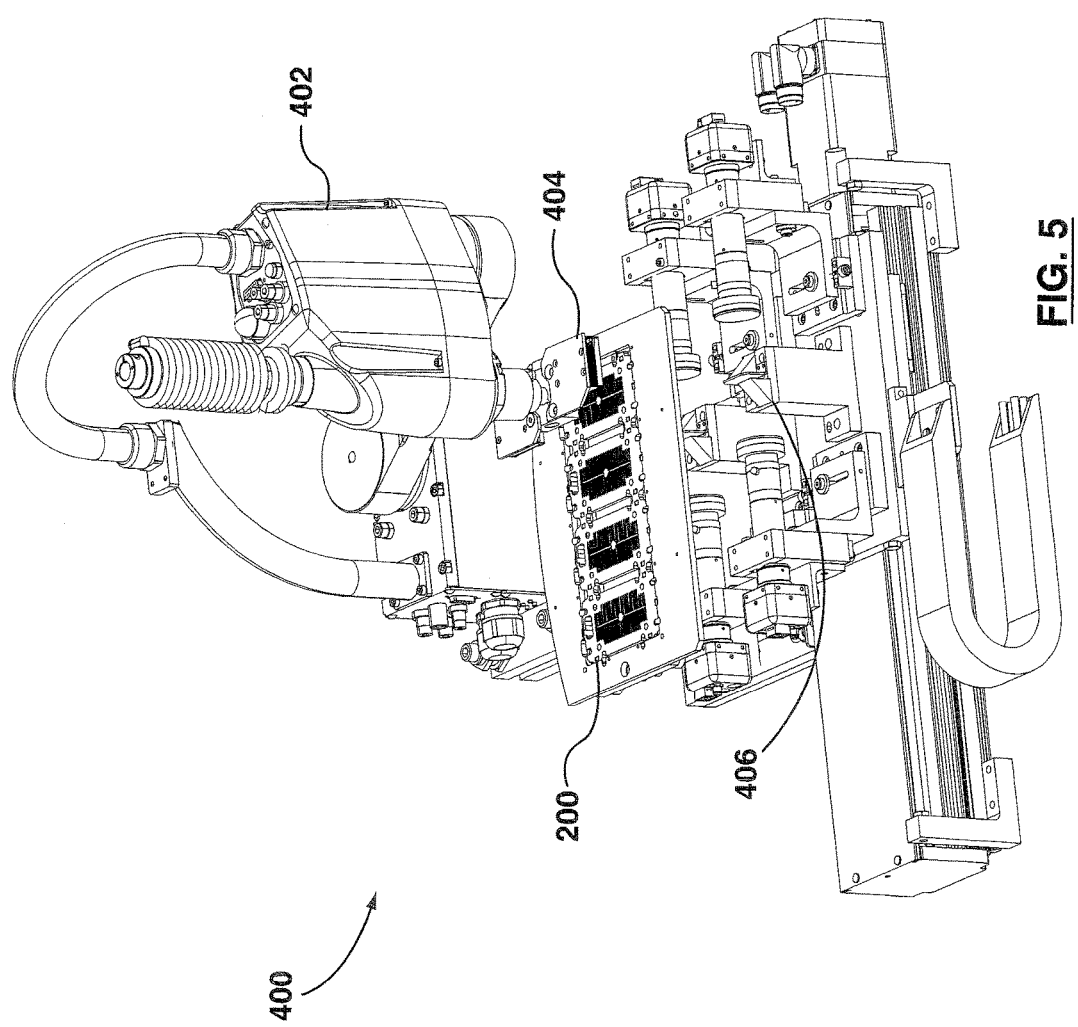
FIG. 5 is a perspective view of an embodiment of a multi-part registration station.

Another embodiment of a registration station, using visual registration, is shown in FIG. 5. In the example of FIG. 5, the registration station 400 includes a robot 402, an end-of-arm tooling 404, a registration camera 406 and a stage 408. The end-of-arm tooling 404 may include, for example, a vacuum gripper, back lights for alignment cameras, mechanical registration features, or the like. The stage 408 may be fixed or may translate with linear motion, planar motion, circular motion, or the like.

If visual registration is used, visual registration may be accomplished by a vision system with one or more cameras placed above or below the pallet thereby allowing the system to incorporate front-lighting or back-lighting. Typically, the positions of the edges of the part are measured for registration purposes; however, other features may also be used as landmarks or indicators. In a multi-pass process, the position of features from previous decoration passes may be measured.

In another embodiment, the registration process may be enhanced by a robotic handler which grasps the individual parts and repositions them relative to the pallet during the registration process. In one embodiment, the robotic handler is a robot with a special gripper.

Generally speaking, the registration process includes registration of the pallet itself with the decoration station and then the individual parts are registered with regard to the decoration station. Registration of the pallet may use any of the registration techniques mentioned above or other known methods. In further cases, the multi-part pallet may be registered prior to receiving the individual parts or at the same time as the registration of the individual parts.

Having multiple part pallets and registration is intended to allow higher throughput of decoration. As described herein, having the pallet, along with the individual parts, all registered is intended to permit the high precision decoration of multiple parts at a given time, or with common decoration passes. This multiple stage registration of the multiple parts is intended to allow for greater throughput of parts and more precise decoration.

After registration, at 106 in the method 100 of FIG. 1, the individual parts are decorated using a concurrent process. The embodiment of the multi-part decoration system 500 shown in FIG. 2, includes a decoration station 502. In an embodiment, a printing template with multiple images related to the positioning of the registered parts within the pallet applies a layer of decoration to the parts as a group. In one implementation, this stage may be implemented via a precision screen printing system. By having the parts individually registered, this stage may be pre-programmed based on the location of parts within the pallet.

In embodiments where a precision screen print station is used, the station may include a precision parallel acting screen printer with servo motion for squeegee action, pressure regulation and lift off. In some cases, the screen print station may be a programmable system capable of complex process recipes incorporating pressure and velocity regulation dependent on the position of the parts. In this case, the screen print station incorporates an interface for precision screen frames. For example, the mechanism may incorporate a precision 2 axis (Y,Z) or (X,Y) motion stage for the squeegee and a precision 1 axis (Z) motion stage for the template. Similarly, an equivalent system may be used with a stencil or a hybrid screen in place of a screen. Other aspects of this type of printing system include mechanical measures or an apparatus for highly repeatable positioning of changeable tooling and coplanarity of the various elements with a well regulated force control. Part contact tooling may be included to avoid marking of surfaces of the product being decorated.

In some embodiments, the decoration station may be configured to have control over various parameters of the decoration process dynamically during the decoration process itself. In one example, the velocities and/or forces present on all three of the independent axes of the screen; control of the X-axis (horizontal), Y-axis (longitudinal) and Z-axis (vertical) may be controlled in order to compensate for different requirements for the decoration on different areas or contours of the part. In a particular case, when the decoration stage performs a lateral print stroke across the parts, the system can concurrently control the height of the screen using the z-axis control. Controlling the z-axis, sometimes referred to as the 'off-contact', can modify the height of the screen or print heads and thus allow finer decoration coverage if the screen or print heads are brought closer to the parts and allow expanded decoration coverage if the screen or print heads are brought away from the parts.

It is also an intended advantage that adjusting the height may allow for fringe coverage over the edge contours of the parts. In an example, bringing the screen to the appropriate height can permit adjustments to decoration coverage such that decoration can be applied at even a ninety-degree edge of a part. Without the change in height, the decoration may be limited to coverage of a flat plane of the part and not its edges. For screen printing, the off-contact may affect the degree of deformation of the screen during printing and the amount of energy with which the screen is pulled away from the ink transferred through the mesh (sometimes called snap-off) following the passage of the print squeegee. Manipulating the degree of deformation by controlling the height of the screen is intended to assist with over-edge printing.

In order to facilitate over edge screen printing, it was determined that the mesh selection of the screen for decoration should be finer. For example, a screen having a higher thread count and small thread diameter than for the flat layer printing. In one example, the screen may have 420 threads-per-inch (TPI) with 30 µm thread versus 380 TPI with 33 µm thread typically used for the flat layer printing. Further, it was determined that the tension for the screen may be set to a lower range than for the flat layer printing. In one example, the screen may have a tension of 24 to 26 N versus 28 to 30 N. Further still, it was determined that the selection of squeegee profile and durometer for the screen printing was a factor that may be considered. A double bevel profile was found to provide more localized deformation of the screen during the print stroke. Lower durometer squeegee material was found to provide more flex of the squeegee to conform to the edge contour of the parts.

In further embodiments, the independent axis control during printing may be used on other types of decoration printing, for example, jet printing.

Further, screens used in the decoration stage, such as for screen printing, are precisely prepared and, in one embodiment, include the use of a very fine mesh with low drag and high tensile strength, careful control of emulsion thickness, precise tensioning to a high and uniform tension, precise registration of screens to frames using specialized fixtures and mask exposure using high precision digital or laser patterning of emulsions. For example, in one application, polyester mesh with 380 mesh and 33 µm threads, possibly Teflon impregnated, may be used, mounted with a diagonal bias. A complex assembly process is used to achieve precise registration of screen to frame along with uniform tension in all directions.

Figure 6:
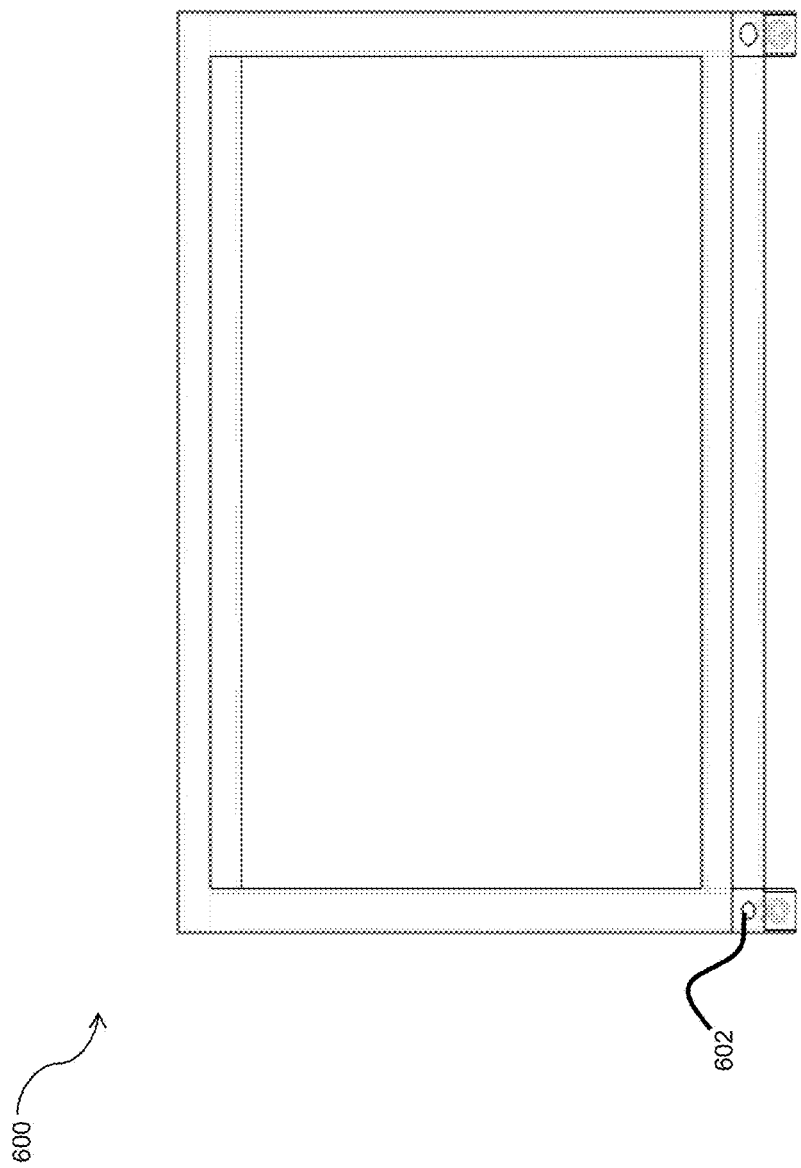
FIG. 6 is a top view of an embodiment of a screen frame.

Screen frames themselves may be made out of a rigid welded structure with precision tooling pin sockets provided as datums. In an embodiment shown in FIG. 6, a screen frame 600 may include registration features to ensure that the screen frame is properly aligned with the parts. Alignment is intended to ensure proper application of the decoration to the parts. In the example of FIG. 6, the screen frame 600 includes oval datum bushings 602. These datum bushings 602 may be used by the registration station to correctly align the screen frames.

Squeegees used in a screen print or stencil process have a complex compliant profile to increase or maximize uniformity of contact pressure and are dressed to a high degree of edge straightness; for example, to better than 25 µm straightness parallel to the template plane. Parallel acting precision pressure control is applied to two points along the length of the squeegee to ensure best parallelism and uniformity of pressure along its length. Note, uniformity of emulsion thickness and penetration in the preparation of screens is also well controlled as is planarity of pallets.

In some embodiments, the system 500 may include a transportation assembly, such as a dial indexer 504, to provide means of transportation of the pallets or fixtures between the various stations 400, 502, 700, 800.

Figure 7:
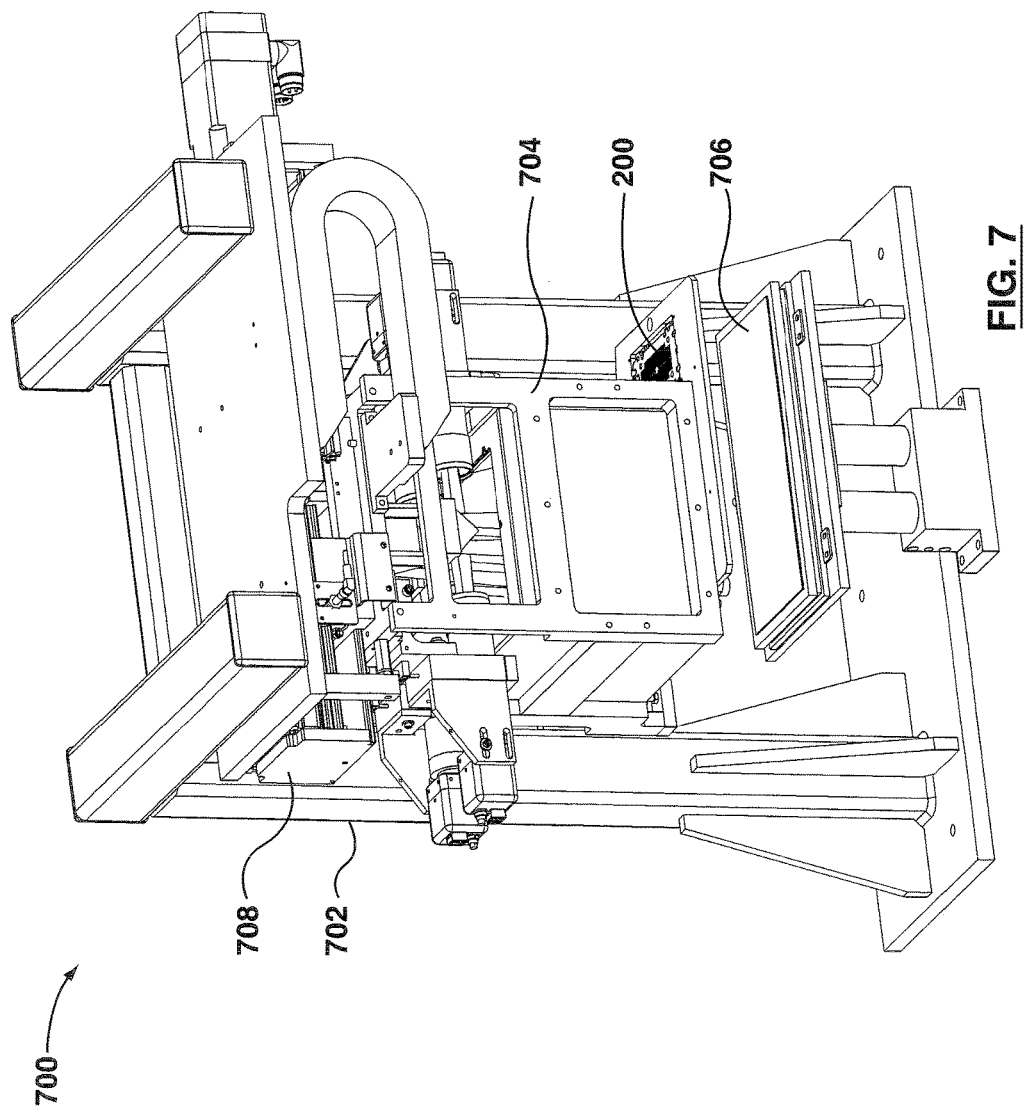
FIG. 7 is a perspective view of an embodiment of a multi-part verification station.

At 108 in the method 100 of FIG. 1, the parts are inspected or verified by various imaging systems. An inspection station 700 is shown in FIG. 7. In the example of FIG. 7, the inspection station 700 includes a support or frame 702, an inspection camera assembly 704, a back lighting assembly 706 and a stage 708. The stage 708 may be fixed or may translate with linear motion, planar motion, circular motion, or the like.

In some cases, the imaging systems enable viewing in reflectance and transmission including specialized optics to measure edge contours and coverage of edge contours. This includes gauging functions that are used to determine fixture offsets for each individual part relative to decoration template images and to manage decoration parameters (feedback functions).

The verification/inspection station 700 may include an imaging system which is capable of examining imaging decoration in front light, backlight, and edge profile. In some cases, this includes uniform backlighting of sufficient quality to determine decoration density at one or more wavelengths. Uniform front light can also be provided in order to examine surface contours. Additional oblique lighting may be incorporated to enable effective imaging of decoration where it wraps around edge contours and may also provide measurement of edge contours. This station is intended to provide high resolution imaging of decoration and, additionally, is configured to make measurements relative to datums on the part pallet. In order to achieve high resolution coverage, cameras may be mounted to motion stages enabling oversize images to be acquired as a series of image captures. Typically, multiple cameras are provided so that multiple parts may be imaged concurrently.

The verification station 700 may incorporate a part handling mechanism in order to expose more or all of the part area for inspection.

In order to achieve the desired precision, in one embodiment, high resolution imaging may be used. Additionally, fixtures and tools are made as precisely coplanar as possible and mechanical registration tooling is high precision. A high degree of mechanical stiffness in each active station and excellent repeatability of tooling is beneficial. Fiducial features on pallets may be precisely formed in order to facilitate visual measurement. An additional feature is the ability to measure print quality with high precision as a means of providing feedback to and regulating the decoration process.

Figure 8:
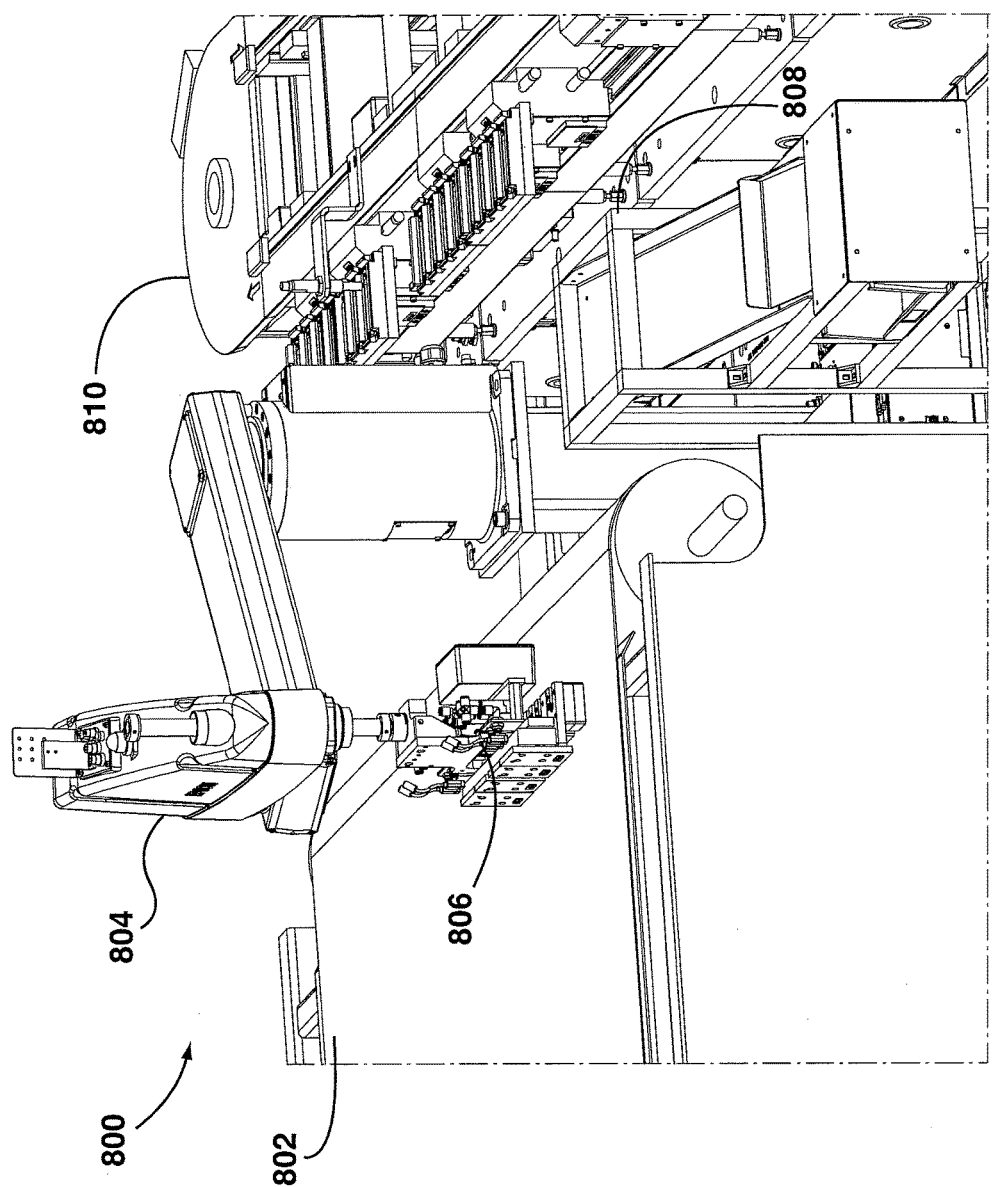
FIG. 8 is a perspective view of an embodiment of a multi-part load/unload station.

At 110 in the method 100 of FIG. 1, the finished, or decorated parts are unloaded. A loading/unloading station 800 is shown in FIG. 8. Rejected parts may be disposed at this stage which may also be seen as a reject station. If a re-circulating transport, or conveyor system 802 is used, this loading/unloading station 800 may be combined with the first (loading) stage whereby the unloading of decorated parts and then the loading of parts to be decorated may be performed consecutively or concurrently. In further embodiments, the loading station and the unloading station may be separate stations.

In the example of FIG. 8, the loading/unloading station 800 includes a loading/unloading robot 804, a gripper 806, and a rejection chute 808. The unloading/loading station 800 is connected to the rest of the decoration system 500 via, for example, a conveyor 810. The pallets and/or parts can then be transported to another area or system via the conveyor system 802.

In order to achieve an improved level of precision of decoration, the decoration system is intended to provide a highly reproducible translation of pallets and parts from the registration position to the decoration stage/station. This may be provided by a high precision dial indexer with minimal eccentricity or it may be provided by a linear transfer mechanism such as a precision linear stage embedded between conveyor rails or the conveyor system, a conveyor system with precision pallet stops or by a precision pallet positioning system such as a Supertrak™ modular conveyor system provided by ATS Automation Tooling Systems.

In an alternative embodiment, the planarity of pallets is well controlled with every pallet nearly coplanar and, more importantly, all part fixturing within an individual pallet ensuring that all parts are coplanar. In other words, the structure of the pallets is controlled so that the insertion of the parts within the pallets results in a planar surface for travel around the conveyor system.

In one embodiment, it has been found that surrounding each part with a mask support or template can improve uniformity during the decoration process, particularly near the edges of parts. This includes the use of raised lands in the fixtures within the pallet which generally surrounds the positioning of the part thereby constraining the elevation of the template outside of the parts and determining the degree of wrapping at the edges of parts, as well as reducing the amount of stretching required to cover each of the parts with the mask support.

Yet another consideration is that the parts to be decorated can sometimes be relatively thin, for example components of electronic devices; consequently, forces applied by vacuum tooling may distort their shape. As such, vacuum tools can be configured for precise regulation of vacuum forces.

In another embodiment, system configuration may vary by doubling up some tool positions as appropriate; for example, the load and unload stages may be combined, the registration stage 12 may be incorporated into the loading stage 10, or the like. In an alternative embodiment, the decoration process or stage may be performed via tampon printing, jet printing, a precision screen print process or the like.

When part thickness is sufficiently variable to detract from coplanarity between parts in a pallet, the decorating apparatus, such as an applicator, may be segmented into several elements each provided with parallel acting force control providing extra compensation for part variation.

An inspection station may be added for inspection of incoming parts prior to decoration or loading of the part onto the pallet.

Various configurations of fixturing within the pallets may be used to facilitate the overall process. For example, pallets may be made partly or mostly transparent or translucent in order to facilitate imaging with less part handling or to improve the inspection process.

Lighting may be primarily monochromatic or may be multispectral. In one example, where the decoration incorporates partially transparent material, e.g. infra-red (IR) transparent or the like, and multiple layers are stacked over each other, it may be beneficial to have this type of lighting. In other examples, this may facilitate verification of multicolor decoration.

An alternate system may also be provided where the various decoration passes are performed sequentially, i.e. the application of multiple layers, possibly with drying/curing stations in-between decoration stations or multiple repeats of the decoration stage.

In another embodiment of the disclosure, described with respect to the method outlined above in FIG. 1, the method may include registering the multiple parts in a pallet individually such that reference features on the part are precisely coordinated to each of the images in the decoration template (e.g. screen print mask). In other words, the registration stage may be used to assist in aligning the decoration template with the positioning of the parts within the pallet to improve and facilitate the decoration stage. All parts within a pallet may then be decorated concurrently. Subsequently, parts are examined for quality and placement of decoration relative to reference features with results being used to monitor and adjust the process by feeding the inspection results back to the decoration stage.

In some cases, in a preparatory process stage, which may be seen as a calibration stage, each pallet is presented to the inspection station and its landmarks (fiducials) located. This allows differences or variations between pallets to be captured and stored so that these variations may be applied as pallet/cavity specific corrections during the decoration process. This preparatory stage is intended to reduce or minimize the effect of differences in pallets and most transport errors so that the decoration of the parts may be improved. Since parts are registered relative to pallet landmarks (fiducials), this is intended to reduce or eliminate the critical motion to the repeatability of pallet motion between registration and decoration stages.

Template precision of the templates is generally improved by preparatory processes which are performed prior to installation into the system but which has significant impact on the actual process. For example, screen preparation may include precise application of emulsion controlling thickness and penetration, precise digital imaging to produce the mask while maintaining a controlled tension and precise mounting of the screen to the frame using mask datums to position the screen to frame datums. Screens and templates can be inspected for image offsets to mechanical (frame) datums, aperture dimensions and tension.

Prior to operation (seen as the method in FIG. 1), a template may be mounted to the system using mechanical datums such as tooling pins, kinematic fixture mounts, etc. This establishes a repeatable relationship between the template and the material handling system. Optionally, the height of the template relative to fixtured parts may be calibrated. Templates may incorporate traceability features which link to pedigree data obtained at the preparation step; this information may be captured and used to preset the system to accommodate template characteristics.

Exact locations of template images may be calibrated using blanks, dummy parts or sacrificial parts that may be decorated and measured in order to determine the relationship between template images and pallet datums. This assists to establish working offsets for each individual part position. Parts are imprinted and then inspected by the inspection station to determine the offset of the pattern relative to the fixture landmarks or fiducials. This is intended to capture any variation of one template to another, and thus maintain reproducibility when templates are changed out. This also establishes offsets of each individual part location needed to achieve best or an improved placement of decoration relative to each part and may further be applied on a pallet by pallet basis if the reproducibility of pallet motion includes a pallet specific component.

Furthermore, prior to operation, the decoration system may be primed. In one priming method, this may entail decorating blanks, dummy parts or sacrificial parts, possibly including some extra decoration cycles and then inspecting for process quality. The priming may be performed whenever a template (screen) is changed, an applicator (squeegee) is replaced or when the ink supply is replenished. The priming operation may be continued until acceptable and repeatable results are obtained so that the number of errors may be reduced.

After the preparatory stage has been completed, a first stage in production may be performed, which, as outlined in FIG. 1, is to load 102 parts into a pallet. After being loaded into the pallet, the parts may be roughly registered 104 by various methods or merely supplied in a relatively well ordered stream (in trays for example). The process of loading may incorporate visual or mechanical registration or both. In an embodiment, fine alignment may be unnecessary as the subsequent process step provides the precision part registration needed; in any case, the reference for registration can be different for different decoration passes and this diversity is incorporated in the registration step following.

The stage of registration 104 includes locating reference features on each individual part as well as reference features on the pallet and then repositioning the part accordingly. At this stage, the necessary offsets to cause the part to be aligned to the template are applied.

The registration requirement may be considered variable whereby it is typically dependent on the process pass or operation. Depending on the decoration system, different methods and apparatus for registering parts are contemplated. In the case where layer to layer placement is most important, mechanical registration may be best. In the case where centering on variable size parts or alignment of the current layer to a previous layer is required, visual registration may be used. In some cases, both mechanical and visual registration may be used either consecutively or simultaneously.

Typically, registration involves the application of offsets which places each individual part in the pallet in a position where it is coordinated with the known offsets of the related template image, the template image being the image by which the decoration of the part is administered. Therefore, in order to improve the accuracy of the decoration and to reduce the number of parts which are incorrectly decorated, the stage of registration causes the parts to be moved to locations where they are expected to align with the decoration template.

In one mechanical registration process, parts are biased against mechanical features in order to establish a reference position. In one example, parts are lifted from the pallet and held by a vacuum fixture. They are then driven against a mechanical fixture, possibly a straight edge, a corner, two or three tooling pins, etc. . . . which establishes a fixed location of the part as it slides on the tool. The part is then backed away from the mechanical reference and placed back into the pallet, possibly applying an offset for coordination with the template image. Alternately, the mechanical feature can be advanced and retracted to accomplish a similar result. This has the advantage of speed and can allow several parts to be registered concurrently if redundant tooling is used. The mechanical features may be presented above the pallet or can be presented from below, for example, by inserting pins through apertures in the pallet.

In an alternative mechanical registration process, mechanical features advance to engage the part, typically in a pincer movement, to reposition the part on or within the pallet. The part slides on the pallet but vacuum may be released or even reversed to create an air bearing while the part is being moved. In order to establish a repeatable position for each new part; however, an offset may be applied if this mechanism is capable of adjusting its position.

While mechanical registration is generally effective for simple part references such as outside edges of the part or holes, more complex references may be better handled using visual registration. In one example of a visual registration process, features on the part are located and the part is repositioned accordingly. If the part is picked from the fixture, registered, realigned and then placed, sliding motion is avoided as is contact with the edges of the part which is sometimes undesirable. Alternatively, the part may be engaged by tooling which moves it around while remaining supported on the fixture.

Where the elevation of parts as presented is substantially variable, this may be an additional aspect of part registration. This could be implemented as an additional function of a visual registration system or could use a separate optical or mechanical probe. This could be used for tracking or adjusting pallet variation and may be useful for adjusting to part variation unless part positions are disposed in the same general direction as print application. Alternately, this may provide an error prevention function by ensuring that improperly seated parts are not processed resulting in decoration defects and/or tool damage.

The decoration process or stage 106 may include using the template to impart a patterned layer of material onto each part. The screen or stencil print process is a dynamic process where the pressure applied to the squeegee, the velocity of the squeegee and the height of the template above the part are parameters used in the decoration process. In some applications, the ability to decorate not only the top face of a part but also the edge contours as well (e.g a chamfer or radius) adds a degree of difficulty to the process. A secondary consideration may be that any impact between the printing tools and the edges of the parts can negatively impact quality or accelerate wear out of these items or both. Also, the amount of decoration per linear area may vary significantly. In order to obtain results that are closer to what is desired, i.e. uniform coverage with no voids or bleeds while maximizing template lifetime, precise control of the process may be required.

It has been found that surrounding each part with a mask support improves uniformity, particularly near the edges of parts. Additionally, varying template elevation (referred to as off-contact) based on location relative to the transverse edges of parts is beneficial. Additionally, modulating velocity and/or pressure near high transitions in coverage is beneficial. One aspect of the process is executing a dynamic recipe that varies with position relative to the parts and the distribution of decoration patterns.

In addition to controlling applicator compression and velocity, the off-contact height of the template (the height to which the template rebounds when compression is released) may be a factor; consequently the height of the template may be precisely controlled and may be varied to accommodate part and pallet variations as well as decoration pattern variation; that is, it may be varied for different artworks, inks or passes and may also be varied during a pass.

It is known that even with a good process, some drift can occur over many part cycles, one factor is rheology and volume of the decoration material. This may be compensated through process feedback—adjustments to the recipe parameters—from the subsequent inspection process or stage 108. Equally, as templates wear, stretching or uneven erosion can occur resulting in small shifts in the placement of the decoration on the parts which can be compensated by adjusting offsets to counter the trends.

Decoration can be specialized in several ways, the most common being multi-color printing. In some applications, portions of the decoration may be transparent to selected wavelengths only; for example, to provide an 'invisible' aperture for infrared emitters and receivers in the cover of an electronic device. In such cases, determining the quality of this selective decoration can make use of two or more spectral bands, for example, by use of switchable lighting. In another example, some decoration may be light sensitive, for example, providing coloration when illuminated appropriately (by a blue backlight for example). Again, full inspection may be accomplished by using multispectral imaging in order to obtain a more complete result.

The inspection stage 108 may be quite complex as it performs multiple functions including, but not limited to, quality and process control. As noted above, an embodiment of the inspection station 700 is shown in FIG. 7. Firstly, part quality is verified immediately after the decoration process. The verification/inspection typically includes parameters such as the registration of decoration to reference features on the part, coverage including opacity, voids and smear, and surface quality relating to smoothness and reflectance of the surface. The inspection is intended to provide an apparatus or method of removing poor quality parts from the output stream. The inspection stage is also intended to provide a mechanism for calibrating systematic offsets which can be compensated out including variation in template image locations from template to template and variation in part positions from pallet to pallet which, in turn, may be used to adjust part position in order to improve the registration of decoration features to the product. Additionally, densitometry or other thickness gauging methods may be used to qualify the decoration process and may be further used as feedback to control the decoration process recipe and inking process. Additional advantages such as trending of attributes such as edge erosion and thickness uniformity in order to predict decoration tooling service and replacement may be realized.

Another aspect of the inspection process is to provide up to 100% inspection of up to 100% of each part. This may require high resolution coverage of all edge features and sufficient resolution of solid areas to detect voids and pits. One other consideration is the ability of the inspection system to deal with gloss which is present when decoration layers are still wet. In one example of this inspection process, multiple images are acquired from one or more cameras under multiple lighting conditions including for example, one or more of backlighting, oblique lighting and edge lighting using one or more spectral bands for each. In some cases, cameras or lighting, or both may be moved relative to the parts in order to cover the full area with the desired resolution. In this embodiment, it is assumed that current precision screen print technologies can be performed to a spatial precision of better than 70 µm and thickness to better than 25 µm while similar methods such as stencil printing may achieve even better results; consequently, the inspection system may be required to provide a gauge capability which is commensurate. Similarly, localized defects greater than 75 µm may be classified as 'visible' defects which must be detected where decoration has a cosmetic aspect.

Accurate inspection of edge contour coverage may include the provision of specialized directional lighting which permits, or causes, edge contour features, including defects, to be separated from decoration. One result is that the inspection process may distinguish between coverage variations that result from process variation and those that are induced by variations in edge contour. This may be facilitated through the use of variably polarized lighting. When very thin transparent or semi-transparent films are applied, layer thickness may be resolved by polarametric imaging.

Screen/stencil preparation includes the inspection of finished items for quality. The parameters which may be used for determining part or decoration quality, may include, for example, registration to frame, pattern shrink and swim, mask thickness, tension and tension uniformity. In addition to qualifying good templates, this data can be saved in a traceable pedigree file which may be used to preset process parameters when a new template is installed.

Another advantage of the present embodiments is that they may provide detailed monitoring about the efficiency or accuracy of some of the states or the entire process. The inspection system gauges various parameters such as voids, smears and thickness which can be indicative of inking process issues, particularly applicator compression and off-contact height which can be adjusted. Trending of pattern edge quality and aperture size may be an indicator of template wear. Pattern wander indicates loss of tension which can be trended and adjusted. Systematic or clustered voids may be an indication of contamination which requires a service cycle in order to retain quality. With some inks, bubbles indicate separation of the ink indicating that the supply should be replenished.

In some applications, concentricity or centering of the applied decoration is one of the useful attributes. If the template develops a directional wear pattern, process adjustment may include adjustments to maintain the desired alignment thereby extending the useful lifetime of the template.

Embodiments of the decoration method and system may also be configured to determine layer thickness. In some cases, where decoration is applied to a transparent, translucent or highly reflective part, densitometry may be used to estimate layer thickness. When layers are superposed, and the layers are different, spectral imaging may be used to better refine the measurement of superposed layer thickness and/or opacity/show-through. In other cases, spectral imaging may be applied in order to better resolve the registration of successive layers.

In one alternative embodiment, the inspection imaging system may include variable illumination including direct illumination and oblique illumination applied from the back and the front of the parts. This may entail illuminating portions of the part through the pallet fixture. Generally, most of the part should be supported during the decoration process in order to adequately control compression which may be at odds with optical methods when parts are not particularly stiff. In order to counteract this, one option may be to use transparent or translucent fixtures while another option may be to lift the parts off of the fixture, or pallet, for better visibility. Alternatively, the surface of the fixture holding the parts in the pallet may be made substantially reflective, which may be sufficient for measurements of layer opacity/thickness. These considerations apply mainly to transparent or translucent parts.

In some embodiments, the inspection imaging resolution to be used may require the use of multiple cameras, movable cameras or the like. For example, precision screen printing is expected to provide reproducible patterns to better than 75 µm; consequently, image resolution to better than 25 µm, requiring moderate interpolation, may be desirable. For a 100 mm square part, an image containing at least 20 MPix would provide full coverage and would be needed for each part in the fixture. Since this may not be practical, cameras may be mounted to a motion stage in order to increase the total coverage possible for a given resolution. The motion stage, in turn, may be configured to provide reasonably high positioning accuracy such as ⅕th pixel if interpolated (sub-pixel) measurements are made. Given the need for variable illumination with multiple image captures, fast cameras may be required. If inspection becomes a cycle time bottle neck, one or more cameras may be designated for every part in a pallet.

A further consideration may be that decoration is often cosmetic; thus, the limit of human eye resolution, which is approximately 75 µm, can be considered as a reference dimension for cosmetic defects, independent of decoration process repeatability.

In the embodiments disclosed herein, advantages are intended to include a process setup and adjustment which is mostly automatic, adaptive and quick; systematic errors may be quickly caught reducing runs of reject parts; high levels of precision may be achieved without relying on operator skill; and a high throughput of decorated parts.

The embodiments are intended to provide the ability to position parts accurately relative to template patterns and to determine the offset of template patterns relative to fixturing within a pallet to enable precise contouring of process parameters relative to the line of application. This is particularly useful in controlling the quality of decoration close to the leading and trailing edges of parts.

Overall, establishing a high degree of repeatability and reproducibility in the process is a factor in achieving a high degree of precision. This generally begins with reproducible manufacture of templates followed by precision control of the decoration process. Precise registration of parts to the current template on a part by part, part to template image basis is intended to result in a highly repeatable process facilitating use of SPC methods. One aspect of this system and method is the ability to register both the parts and the template images individually (as opposed to merely aligning a few 'global' fiducials on the template and fixturing). This is beneficial in improving or maximizing the usable lifetime of the template, particularly tolerating drift in the template geometry over time without loss of registration to each part position.

Transfer of parts between registration and decoration is intended to be a beneficial sub-process. This system is intended to transfer very repeatably but allow for small differences between pallets to be accommodated, such as through calibration.

Continuous process monitoring and adjustment permits process quality to be maintained over a protracted interval in spite of reasonable template and applicator wear. The overall result is intended to allow the process to maintain precision of the process to within the technical limits of the template for the life of the template.

Also, detailed visual inspection enables a complex understanding of process performance in real time and provide feedback to other modules/stations in the process and system. For example, registration offsets can be based on optimization of a complex set of features and can apply soft datums such as, for example, feature concentricity, edge clearance, parallelism, and the like, if desired.

In an alternative embodiment, tampon printing may be used as the decoration process. In this case, material is transferred from a print block to the part using a compressible soft tool (tampon). This process is better adapted to uneven and contoured parts. Otherwise, in a precision process most of the same considerations as for screen or stencil printing apply, to the extent that the same basic system and methods may be used. Masters are in the form of plates, consequently, tension is generally not a parameter, however, the various template geometry and possible pedigree data are. Inking is a separate process from imprinting with both processes ideally programmably controlled. Similar considerations such as ink applicator parallelism, compression and velocity apply. Tampon travel (from template to part), force and velocity profiles are also similar. Template wearout has a similar but inverted wear out characteristic (elements grow smaller rather than larger through erosion).

Another alternative for the decoration process is drop-on-demand printing sometimes known as digital printing, ink-jet printing, or the like. In this case, the template is electronic rather than physical. Defects are similar but with some differences; for example, replace smear with spatter. On the one hand, this printing method is more flexible; however, the thickness of material that may be deposited (at least in a single pass) is less, particularly when compared to stencil printing. With this printing technique, it may be possible to adjust the template for each individual part location dynamically, thus reducing or eliminating the need to physically reposition parts after registration. Generally speaking, the same overall process can be applied. In this case, it may be a desirable function to control the fly height of the print heads to the height of the parts based on registration and/or post decoration inspection.

Turning to FIG. 9, a method 900 for controlling a print head, screen or other printing/decorating element during decoration is shown. In this example, reference is made to screen printing but other types of printing may be controlled similarly, as appropriate. At 902, the decoration process is started when the pallet with the parts reaches the decoration station. The pallet may be transferred to the decoration station, after positioning of the parts, by, for example, the registration station. At 904, the screen printer begins its print stroke by translating across the parts along the x-axis, or in other cases, along the y-axis. At 906, the decoration station adjusts the z-axis (height) of the screen as the screen printer translates across the parts. The z-axis of the screen is adjusted based on predetermined factors or characteristics during the motion along the x-axis or y-axis. Adjusting the height of the screen may allow for finer decoration coverage if the screen is brought closer to the parts, and allow less defined and/or expanded decoration coverage if the screen is brought away from the parts. Adjusting the height of the screen is intended to allow for fringe coverage as the printer approaches and encounters the edges of a part. As noted, the z-axis is adjusted based on predetermined characteristics, which may include, for example, the shape of the parts, the edge profiles of the parts, holes or other features in the parts, the decoration coverage, the decoration type, the decoration quality, or the like.

After the decoration has been applied by the screen printer, at 908, the parts are inspected by the inspection station. The inspection may provide updated predetermined characteristics on which the z-axis motion of the print stroke is based. Based on the predetermined characteristics determined after inspection, at 910, the decoration station determines whether the z-axis motion of the print stroke needs to be adjusted. If it is determined based on the predetermined characteristics that the z-axis motion needs to be adjusted, at 912, the decoration station adjusts the z-axis motion. Then, at 902, the decoration process is commenced again for subsequent print strokes on the same parts, or for decoration of subsequent parts. The adjusted z-axis motion ensures that subsequently decorated parts receive the required decoration coverage and quality. If the z-axis motion does not need to be adjusted, then, at 902, the decoration process is commenced again for subsequent print strokes on the same parts, or for decoration of subsequent parts.

In some cases, the method may use a prescribed master slave relationship between the print stroke (x-axis or y-axis) and the off-contact gap (z-axis). In this case, the programmable motion, such as a servo motion cam profile of the z-axis control, may be updated between print cycles based on the inspection feedback.

While the general description may imply that the multiple parts are identical parts, they could equally be a group or groups of different parts, perhaps several components of an assembly.

In the preceding description, for purposes of explanation, numerous details are set forth in order to provide a thorough understanding of the embodiments. However, it will be apparent to one skilled in the art that specific details may not be required. In other instances, well-known structures are shown in block diagram form in order not to obscure the understanding. For example, specific details are not provided as to whether the embodiments described herein or elements thereof are implemented as a software routine, hardware circuit, firmware, or a combination thereof.

Embodiments of the disclosure or elements thereof can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A method of decorating multiple parts, the method comprising:
    inspecting a plurality of pallets at an inspection station to determine landmarks associated with each pallet;
    loading a plurality of parts onto each of the plurality of pallets, via a loading station;
    registering location of each of the plurality of parts in relation to each of the pallets, via a registration station, wherein registering location of each of the plurality of parts comprises visual and mechanical registration, based on relative alignment of the part to the pallet using the pallet landmarks;
    registering location of each of the plurality of parts with each of a plurality of templates, wherein registering location of each of the plurality of parts with each of a plurality of templates comprises visual and mechanical registration based on the registering location of each of the plurality of parts in relation to the pallet in three independent axes, and adjusting a height of a template to allow for fringe coverage over at least one edge of at least one part;
    decorating the plurality of parts using the plurality of templates, via a decoration station;
    inspecting the decorated plurality of parts to monitor for defects, via the inspection station, wherein the inspection station comprises a camera assembly, a back lighting assembly, an oblique lighting assembly and a stage, and inspecting the decorated part comprises:
        backlighting the decorated parts to determine decoration density at one or more wavelengths, via the back lighting assembly; and
        oblique lighting the decorated parts to enable imaging of decoration when the decoration wraps around edge contours of the part, via the oblique lighting assembly; and
    providing feedback from the inspecting the decorated plurality of parts to the registering location of each of the plurality of parts in relation to each of the pallets and the registering location of each of the plurality of parts with each of the plurality of templates.

2. The method of claim 1 wherein registering location of each of the plurality of parts comprises:
    locating reference features on each of the plurality of parts, wherein the reference features are coordinated to each of the plurality of templates;
    locating reference features on the pallet; and
    aligning the respective reference features to position each of the plurality of parts in relation to the pallet, wherein aligning comprises determining an offset to cause the part to be aligned to each of the plurality of templates.

3. The method of claim 2, further comprising:
    adjusting an alignment based on feedback from the inspecting in order to compensate for defects or variance.

4. The method of claim 1 wherein registering location of each of the plurality of parts with each of the plurality of templates comprises:
    locating reference features on each of the plurality of templates;
    locating reference features on the pallet or on each of the plurality of parts; and
    aligning the respective reference features to align each of the plurality of templates in relation to each of the plurality of parts.

5. The method of claim 4, further comprising:
    adjusting the alignment based on feedback from the inspecting in order to compensate for defects or variance.

6. The method of claim 1 wherein the decorating comprises:
    monitoring the decorating; and
    adjusting one or more parameters of the decorating during the decorating to provide for enhanced print coverage.

7. The method of claim 6, wherein the adjusting one or more parameters comprises adjusting off-contact during decorating.

8. The method of claim 1 wherein the inspecting comprises:
    providing predetermined illumination characteristics;
    capturing images with a plurality of cameras; and
    analyzing the images.

9. The method of claim 1, wherein the pallets are transparent.

10. A system of decorating multiple parts, the system comprising:
    a loading station for loading a plurality of parts onto a pallet of a plurality of pallets, wherein the parts are held to the pallet through vacuum fixtures;
    a registration station for registering a location of each of the plurality of parts in relation to each of the pallets and for registering a location of each of the plurality of parts with each of a plurality of templates, wherein registering location of each of the plurality of parts and registering location of each of the plurality of parts with each of a plurality of templates comprises visual registration with a vision system and mechanical registration with a mechanical registration assembly and wherein registering location of each of the plurality of parts comprises registering location using relative alignment in three independent axes of the part to the pallet using pallet landmarks by aligning features in the plurality of parts or plurality of templates with features in the plurality of pallets with a robotic handler, and adjusting a height of a template with a motion stage to allow for fringe coverage over at least one edge of at least one part;

a decoration station for decorating the plurality of parts using the plurality of templates; and an inspection station for inspecting the decorated plurality of parts to monitor for defects, wherein the inspection station comprises:
a camera assembly,
a back lighting assembly configured to backlight the decorated parts to highlight decoration density of each of the plurality of parts at one or more wavelengths;
an oblique lighting assembly configured to light the decorated parts to enable imaging of decoration when the decoration wraps around edge contours of the part; and
a stage;

wherein the inspection station provides feedback from the inspecting the decorated plurality of parts to the registration station regarding the registering location of each of the plurality of parts in relation to each of the pallets and the registering location of each of the plurality of parts with each of the plurality of templates.

11. The system of claim 10, wherein the registration station registers the location of each of the plurality of parts by:
locating reference features on each of the plurality of parts, wherein the reference features are coordinated to each of the plurality of templates;
locating reference features on the pallet; and
aligning the respective reference features to position each of the plurality of parts in relation to the pallet.

12. The system of claim 11, wherein the registration station adjusts an alignment based on feedback from the inspecting at the inspection station in order to compensate for defects.

13. The system of claim 10 wherein the registration station registers the location of each of the plurality of parts by:
locating reference features on each of the plurality of templates;
locating reference features on the pallet or on each of the plurality of parts; and
aligning the respective reference features to align each of the plurality of templates in relation to each of the plurality of parts.

14. The system of claim 13, wherein the registration station adjusts the alignment based on feedback from the inspecting at the inspection station in order to compensate for defects.

15. The system of claim 10, wherein the decoration station:
monitors the decorating; and
adjusts one or more parameters of the decorating during the decorating to provide for enhanced print coverage.

16. The system of claim 10, wherein the pallets are transparent.

* * * * *